US011825819B2

(12) United States Patent
Gonzaga-Jauregui et al.

(10) Patent No.: US 11,825,819 B2
(45) Date of Patent: Nov. 28, 2023

(54) *CRNN* LOSS OF FUNCTION RODENT MODEL

(71) Applicant: REGENERON PHARMACEUTICALS, INC., Tarrytown, NY (US)

(72) Inventors: Claudia Gonzaga-Jauregui, Elmsford, NY (US); Sokol Haxhinasto, Brookfield, CT (US); Zaruhi Hovhannisyan, Hoboken, NJ (US); Kavita Praveen, New York City, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 427 days.

(21) Appl. No.: 17/061,978

(22) Filed: Oct. 2, 2020

(65) Prior Publication Data
US 2021/0100227 A1 Apr. 8, 2021

Related U.S. Application Data

(60) Provisional application No. 62/909,982, filed on Oct. 3, 2019.

(51) Int. Cl.
*A01K 67/027* (2006.01)
*A61K 49/00* (2006.01)

(52) U.S. Cl.
CPC ...... *A01K 67/0276* (2013.01); *A61K 49/0008* (2013.01); *A01K 2217/054* (2013.01); *A01K 2217/056* (2013.01); *A01K 2227/105* (2013.01); *A01K 2267/0368* (2013.01)

(58) Field of Classification Search
None
See application file for complete search history.

(56) References Cited

U.S. PATENT DOCUMENTS

| | | | |
|---|---|---|---|
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 8,354,389 B2 | 1/2013 | Frendewey et al. | |
| 8,518,392 B2 | 8/2013 | Frendewey et al. | |
| 8,697,851 B2 | 4/2014 | Frendewey et al. | |
| 2008/0078000 A1 | 3/2008 | Poueymirou et al. | |
| 2014/0235933 A1 | 8/2014 | Lee et al. | |
| 2014/0310828 A1 | 10/2014 | Lee et al. | |

FOREIGN PATENT DOCUMENTS

| | | |
|---|---|---|
| CN | 106620694 A | 5/2017 |
| WO | 2019/079238 A1 | 4/2019 |

OTHER PUBLICATIONS

Liedén, A. (2007). Gene Expression and Genetic Association Studies in Eczema [Doctoral Dissertation, Karolinska Institutet]. Reproprint. (Year: 2007).*
Thorn, K. Genetically encoded fluorescent tags. Molecular Biology of the Cell (2017) 28:7, 848-857. (Year: 2017).*
Contzler R. et al., "Cornulin, a New Member of the "Fused Gene" Family, is Expressed During Epidermal Differentiation", J Invest Dermatol 124: 990-997 (May 5, 2005).
Feng B-J et al., "Genotype and Phenotype Analyses Revealed Novel Susceptibility Genes and New Clinical Classification for Psoriasis", American Society of Human Genetics 67th Annual Meeting (Oct. 17-21, 2017), Abstract.
Flutter B. et al., "TLRs to Cytokines: Mechanistic Insights from the Imiquimod Mouse Model of Psoriasis", European Journal of Immunology 43:3138-3146 (2013).
Frendewey D. et al., "The Loss-of-Allele Assay for ES Cell Screening and Mouse Genotyping", Methods in Enzymology 476:295-307 (2010).
Kanneganti T-D et al., "Bacterial RNA and Small Antiviruai Compounds Activate Caspase-1 Through Cryopyrin/Nalp3", Nature 440:233-236 (Mar. 9, 2006).
Li C. et al., "Cornulin is Induced in Psoriasis Lesions and Promotes Keratinocyte Proliferation Via Phosphoinositide 3-Kinase/Akt Pathways", Journal of Investigative Dermatology 139:71-80 (2019).
Nakajima K. et al., "Mouse Models of Psoriasis and Their Relevance", Journal of Dermatology 45:252-263 (2018).
Poueymirou W T et al., "F0 Generation Mice Fully Derived from Gene-Targeted Embryonic Stem Cells Allowing Immediate Phenotypic Analyses", Nature Biotechnology 25(1):91-99 (Jan. 2007).
Roberson E.D.O. et al., "Psoriasis Genetics: Breaking the Barrier", Trends in Genetics 26:415-423 (2010).
Swindell W.R. et al., "Genome-Wide Expression Profiling of Five Mouse Models Identifies Similarities and Differences With Human Psoriasis", PLoS One 6(4):e18266 (Apr. 2011).
Valenzuela D.M. et al., "High Throughput Engineering of the Mouse Genome Coupled With High-Resolution Expression Analysis", Nature Biotechnology 21(6):652-659 (Jun. 2003).
Van Der Fits L. et al., "Imiquimod-Induced Psoriasis-Like Skin Inflammation in Mice is Mediated Via the IL-23/IL-17 Axis", The Journal of Immunology 182:5836-5845 (2009).
NCBI Reference Sequence No. NM_016190.3 (6 pages) (Dec. 11, 2020).
NCBI Reference Sequence No. NP_057274.1 (3 pages) (Dec. 11, 2020).
NCBI Reference Sequence No. NM_001081200.2 (4 pages) (Oct. 7, 2020).
NCBI Reference Sequence No. NP_001074669.1 (3 pages) (Oct. 7, 2020).

(Continued)

*Primary Examiner* — Allison M Fox
*Assistant Examiner* — Alyssa G Weston
(74) *Attorney, Agent, or Firm* — Scully, Scott, Murphy & Presser, P.C.; Haiou Qin

(57) ABSTRACT

This disclosure relates to a genetically modified rodent and use thereof as a rodent model. More specifically, this disclosure relates to rodent (e.g., mouse or rat) comprising a loss of function mutation in an endogenous Crnn (cornulin) gene, and to use of such a rodent animal as a rodent model of skin inflammation disorders (e.g., psoriasis).

13 Claims, 6 Drawing Sheets
(6 of 6 Drawing Sheet(s) Filed in Color)
Specification includes a Sequence Listing.

(56) References Cited

OTHER PUBLICATIONS

NCBI reference Sequence No. XM_227367.6 (4 pages) (Jul. 26, 2016).
NCBI Reference Sequence No. XP_227367.5 (3 pages) (Jan. 21, 2021).
Bouabe H. et al., "Gene Targeting in Mice: A Review", Methods Mol Biol. 1064:315-336 (2013).
Chen J. et al., "Genetically Engineered Mouse Models for Skin Research: Taking the Next Step", Journal of Dermatological Science 52(1):1-12 (Oct. 2008).
Devoy A. et al., "Genomically Humanized Mice: Technologies and Promises", Nature 13:14-20 (Jan. 2012).
International Search Report and Written Opinion dated Jan. 20, 2021 received in International Application No. PCT/US2020/053994.

* cited by examiner

SEQUENCE LISTING

<160> NUMBER OF SEQ ID NOS: 6

<210> SEQ ID NO 1
<211> LENGTH: 1902
<212> TYPE: DNA
<213> ORGANISM: Homo sapiens

<400> SEQUENCE: 1

| | | | | | | |
|---|---|---|---|---|---|---|
| actcctcaca | ccacttaaca | gccacttgtt | tcatcccacc | tgggcattag | gttgacttca | 60 |
| aagatgcctc | agttactgca | aaacattaat | gggatcatcg | aggccttcag | gcgctatgca | 120 |
| aggacggagg | gcaactgcac | agcgctcacc | cgaggggagc | tgaaaagact | cttggagcaa | 180 |
| gagtttgccg | atgtgattgt | gaaacccCac | gatccagcaa | ctgtggatga | ggtcctgcgt | 240 |
| ctgctggatg | aagaccacac | agggactgtg | gaattcaagg | aattcctggt | cttagtgttt | 300 |
| aaagttgccc | aggcctgttt | caagacactg | agcgagagtg | ctgagggagc | ctgcggctct | 360 |
| caagagtctg | gaagcctcca | ctctggggcc | tcgcaggagc | tgggcgaagg | acagagaagt | 420 |
| ggcactgaag | tgggaagggc | ggggaaaggg | cagcattatg | aggggagcag | ccacagacag | 480 |
| agccagcagg | gttccagagg | gcagaacagg | cctggggttc | agacccaggg | tcaggccact | 540 |
| ggctctgcgt | gggtcagcag | ctatgacagg | caagctgagt | cccagagcca | ggaaagaata | 600 |
| agcccgcaga | tacaactctc | tgggcagaca | gagcagaccc | agaaagctgg | agaaggcaag | 660 |
| aggaatcaga | caacagagat | gaggccagag | agacagccac | agaccaggga | acaggacaga | 720 |
| gcccaccaga | caggtgagac | tgtgactgga | tctggaactc | agacccaggc | aggtgccacc | 780 |
| cagactgtgg | agcaggacag | cagccaccag | acaggaagaa | ccagcaagca | gacacaggag | 840 |
| gccaccaatg | accagaacag | agggactgag | acccacggtc | aaggcaggag | ccagaccagc | 900 |
| caggctgtga | caggaggaca | tgctcagata | caggcaggga | cacacaccca | gacacccacc | 960 |
| cagaccgtgg | agcaggacag | cagccaccag | acaggaagca | ccagcaccca | gacacaggag | 1020 |
| tccaccaatg | gccagaacag | agggactgag | atccacggtc | aaggcaggag | ccagaccagc | 1080 |
| caggctgtga | caggaggaca | cactcagata | caggcagggt | cacacaccga | gactgtggag | 1140 |
| caggacagaa | gccaaactgt | aagccacgga | ggggctagag | aacagggaca | gacccagacg | 1200 |
| cagccaggca | gtggtcaaag | atggatgcaa | gtgagcaacc | ctgaggcagg | agagacagta | 1260 |
| ccgggaggac | aggcccagac | tggggcaagc | actgagtcag | gaaggcagga | gtggagcagc | 1320 |
| actcacccaa | ggcgctgtgt | gacagaaggg | caggagaca | gacagccac | agtggttggt | 1380 |
| gaggaatggg | ttgatgacca | ctcaagggag | acagtgatcc | tcaggctgga | ccagggcaac | 1440 |
| ttgcatacca | gtgtttcctc | agcacagggc | caggatgcag | cccagtcaga | agagaagcga | 1500 |
| ggcatcacag | ctagagagct | gtattcctac | ttgagaagca | ccaagccatg | acttccccga | 1560 |
| ctccaatgtc | cagtactgga | agaagacagc | tggagagagt | ttggcttgtc | ctgcatggcc | 1620 |
| aatccagtgg | gtgcatccct | ggacatcagc | tcttcattat | gcagcttccc | ttttaggtct | 1680 |
| ttctcaatga | gataatttct | gcaaggagct | ttctatcctg | aactcttctt | tcttacctgc | 1740 |
| tttgcggtgc | agaccctctc | aggagcagga | agactcagag | caagtcaccc | ctttgtactg | 1800 |
| aattgtcctc | atcttgtggg | gggtttcagg | actattttta | tctctgacat | ctctctattg | 1860 |
| ccccatctac | cctaatgcat | caataaaacc | ttaagccact | gg | | 1902 |

<210> SEQ ID NO 2
<211> LENGTH: 495
<212> TYPE: PRT
<213> ORGANISM: Homo sapiens

<400> SEQUENCE: 2

```
Met Pro Gln Leu Leu Gln Asn Ile Asn Gly Ile Ile Glu Ala Phe Arg
1               5                   10                  15

Arg Tyr Ala Arg Thr Glu Gly Asn Cys Thr Ala Leu Thr Arg Gly Glu
                20                  25                  30

Leu Lys Arg Leu Leu Glu Gln Glu Phe Ala Asp Val Ile Val Lys Pro
            35                  40                  45

His Asp Pro Ala Thr Val Asp Glu Val Leu Arg Leu Asp Glu Asp
        50                  55                  60

His Thr Gly Thr Val Glu Phe Lys Glu Phe Leu Val Leu Val Phe Lys
65                  70                  75                  80

Val Ala Gln Ala Cys Phe Lys Thr Leu Ser Glu Ser Ala Glu Gly Ala
                85                  90                  95

Cys Gly Ser Gln Glu Ser Gly Ser Leu His Ser Gly Ala Ser Gln Glu
                100                 105                 110

Leu Gly Glu Gly Gln Arg Ser Gly Thr Glu Val Gly Arg Ala Gly Lys
            115                 120                 125

Gly Gln His Tyr Glu Gly Ser Ser His Arg Gln Ser Gln Gln Gly Ser
        130                 135                 140

Arg Gly Gln Asn Arg Pro Gly Val Gln Thr Gln Gly Gln Ala Thr Gly
145                 150                 155                 160

Ser Ala Trp Val Ser Ser Tyr Asp Arg Gln Ala Glu Ser Gln Ser Gln
                165                 170                 175

Glu Arg Ile Ser Pro Gln Ile Gln Leu Ser Gly Gln Thr Glu Gln Thr
                180                 185                 190

Gln Lys Ala Gly Glu Gly Lys Arg Asn Gln Thr Thr Glu Met Arg Pro
            195                 200                 205

Glu Arg Gln Pro Gln Thr Arg Glu Gln Asp Arg Ala His Gln Thr Gly
        210                 215                 220

Glu Thr Val Thr Gly Ser Gly Thr Gln Thr Gln Ala Gly Ala Thr Gln
225                 230                 235                 240

Thr Val Glu Gln Asp Ser Ser His Gln Thr Gly Arg Thr Ser Lys Gln
                245                 250                 255

Thr Gln Glu Ala Thr Asn Asp Gln Asn Arg Gly Thr Glu Thr His Gly
                260                 265                 270

Gln Gly Arg Ser Gln Thr Ser Gln Ala Val Thr Gly Gly His Ala Gln
            275                 280                 285

Ile Gln Ala Gly Thr His Thr Gln Thr Pro Thr Gln Thr Val Glu Gln
        290                 295                 300

Asp Ser Ser His Gln Thr Gly Ser Thr Ser Thr Gln Thr Gln Glu Ser
305                 310                 315                 320

Thr Asn Gly Gln Asn Arg Gly Thr Glu Ile His Gly Gln Gly Arg Ser
                325                 330                 335

Gln Thr Ser Gln Ala Val Thr Gly Gly His Thr Gln Ile Gln Ala Gly
                340                 345                 350

Ser His Thr Glu Thr Val Glu Gln Asp Arg Ser Gln Thr Val Ser His
            355                 360                 365

Gly Gly Ala Arg Glu Gln Gly Thr Gln Thr Gln Pro Gly Ser Gly
        370                 375                 380

Gln Arg Trp Met Gln Val Ser Asn Pro Glu Ala Gly Glu Thr Val Pro
385                 390                 395                 400

Gly Gly Gln Ala Gln Thr Gly Ala Ser Thr Glu Ser Gly Arg Gln Glu
```

```
                405                 410                 415
Trp Ser Ser Thr His Pro Arg Arg Cys Val Thr Glu Gly Gln Gly Asp
            420                 425                 430

Arg Gln Pro Thr Val Val Gly Glu Glu Trp Val Asp Asp His Ser Arg
        435                 440                 445

Glu Thr Val Ile Leu Arg Leu Asp Gln Gly Asn Leu His Thr Ser Val
    450                 455                 460

Ser Ser Ala Gln Gly Gln Asp Ala Ala Gln Ser Glu Glu Lys Arg Gly
465                 470                 475                 480

Ile Thr Ala Arg Glu Leu Tyr Ser Tyr Leu Arg Ser Thr Lys Pro
                485                 490                 495

<210> SEQ ID NO 3
<211> LENGTH: 1973
<212> TYPE: DNA
<213> ORGANISM: Mus musculus

<400> SEQUENCE: 3
```

| | | | | | |
|---|---|---|---|---|---|
| actctacaca | ctgcttaaca | gaaacttgtc | ccatcctgcc | tgagcattag | catagcttca | 60 |
| aagatgcctc | agttgctgca | aaacatccac | gggatcatcg | aagccttcgg | gtgctatgcc | 120 |
| aggtcagagg | gtggctgcaa | agtactcacg | aggcaggagt | tgaagaggct | cctggaacat | 180 |
| gagtttgctg | acgtcatagt | gaagccccat | gatcctgcaa | ctgtggatga | agtcctgcgc | 240 |
| ctgttggatg | aagataacac | agggactgta | gagttcaagg | aattcctagt | cttggtgttt | 300 |
| aaagttgcac | gggcttgctt | taagacactg | aatgagagtc | ctaagggtgc | ttgcatatct | 360 |
| gacaagtctg | aaggctgcta | ttctggatct | tcaaaagagc | tggagcaaag | acagagaggt | 420 |
| ggtgctgaag | tggcaaaaga | cggagcagca | cagcactgtg | aagacagcag | ctgtggacag | 480 |
| agagatcagg | cttctagagg | acaggacagg | gttgggacac | atacccagaa | tcaggacagc | 540 |
| taccctacac | aggtcagcag | tcatgacagg | cagactgagt | ctcagacaca | ggaaatgata | 600 |
| agccaacaaa | cacaagtgac | aggacaggtg | gagcagaccc | aagaacaga | agacaagagt | 660 |
| tggaccagac | agaagaggtc | agagaggcaa | ccacagagta | gccaacagac | agatgagatc | 720 |
| acaactggat | ctacagctca | gacccaagca | ggtaacttct | acacacaggg | gtctacctgt | 780 |
| gactataaca | gaggaactaa | cagccatcac | caagacagaa | gccatgcaga | cagagcttct | 840 |
| acacaacact | accagacaca | ggcagggtct | catactcaga | tacacacaca | gatggtagaa | 900 |
| caggcctggg | ggcagcaaac | aggaagtgat | agcatccaga | cacaggggtc | tatctatgac | 960 |
| cagagcactg | agactgtgat | tcatggccaa | gacaggaacc | aggcaagcca | gagtgttaaa | 1020 |
| gaacaccacc | aggcacaggg | agagtcatat | attcagacac | atactcagac | aatggaacaa | 1080 |
| ggcaggagcc | agcaggcaga | aaatagtagc | acccagactc | atgggtccat | gtatggccaa | 1140 |
| aacagagaga | ctgagatcca | tgggctagaa | agcagtcagg | cagaacaggt | ggggacaaga | 1200 |
| cactaccaga | cacaggcagg | atcatatacc | cagactttgg | aacatgatgg | gagccagtct | 1260 |
| gcacataaat | ttgtggctca | agaaaaggaa | cgtacacaga | caaagccatg | catggggcaa | 1320 |
| agctggacac | cagtaagcaa | ctatgagaca | gaagagtcag | tgataggagg | acaggtccag | 1380 |
| actgagacag | acactattat | agagaatcac | ccaagcccga | cagccaggca | ggtagagaga | 1440 |
| gtacccacag | tggttagaga | ggagtgggtc | aatgaccaca | aagggaaat | agtaatccga | 1500 |
| agccaggatc | caggtagcct | gcactctggt | actccttcag | ctcagggcca | ggatatacca | 1560 |
| cagatggaga | agaaaggaat | cacagccaag | ggactatata | cctacttgaa | gacagagcag | 1620 |

```
ccatgacttt tcccgattcc agctggagtg aggttggcct gccctgccct gccctgccct      1680
gccctgccct gccctgccct gccctgccct gccatggtac ttcaccagac agccatgatt      1740
cttcttgttt ggttctttta cagtgatcat ctctacaagg tgatttcttg tcaaaactca      1800
cctctcttac ctgctgctct cagaaactca cctctcttac ctgatattct cagaaacagg      1860
aagatgtgga ggaggtcatc tcattgcact gaattccccc caattttcag ggggtttcaa      1920
agctgtttta tctctggtat ctgtccattg catcaataaa ggcttagaag ctg             1973
```

<210> SEQ ID NO 4
<211> LENGTH: 520
<212> TYPE: PRT
<213> ORGANISM: Mus musculus

<400> SEQUENCE: 4

```
Met Pro Gln Leu Leu Gln Asn Ile His Gly Ile Ile Glu Ala Phe Gly
 1               5                  10                  15

Cys Tyr Ala Arg Ser Glu Gly Gly Cys Lys Val Leu Thr Arg Gln Glu
            20                  25                  30

Leu Lys Arg Leu Leu Glu His Glu Phe Ala Asp Val Ile Val Lys Pro
        35                  40                  45

His Asp Pro Ala Thr Val Asp Glu Val Leu Arg Leu Leu Asp Glu Asp
    50                  55                  60

Asn Thr Gly Thr Val Glu Phe Lys Glu Phe Leu Val Leu Val Phe Lys
65                  70                  75                  80

Val Ala Arg Ala Cys Phe Lys Thr Leu Asn Glu Ser Pro Lys Gly Ala
                85                  90                  95

Cys Ile Ser Asp Lys Ser Glu Gly Cys Tyr Ser Gly Ser Ser Lys Glu
           100                 105                 110

Leu Glu Gln Arg Gln Arg Gly Gly Ala Glu Val Ala Lys Asp Gly Ala
       115                 120                 125

Ala Gln His Cys Glu Asp Ser Ser Cys Gly Gln Arg Asp Gln Ala Ser
   130                 135                 140

Arg Gly Gln Asp Arg Val Gly Thr His Thr Gln Asn Gln Asp Ser Tyr
145                 150                 155                 160

Pro Thr Gln Val Ser Ser His Asp Arg Gln Thr Glu Ser Gln Thr Gln
                165                 170                 175

Glu Met Ile Ser Gln Gln Thr Gln Val Thr Gly Gln Val Glu Gln Thr
           180                 185                 190

Pro Arg Thr Glu Asp Lys Ser Trp Thr Arg Gln Lys Arg Ser Glu Arg
       195                 200                 205

Gln Pro Gln Ser Ser Gln Gln Thr Asp Glu Ile Thr Thr Gly Ser Thr
   210                 215                 220

Ala Gln Thr Gln Ala Gly Asn Phe Tyr Thr Gln Gly Ser Thr Cys Asp
225                 230                 235                 240

Tyr Asn Arg Gly Thr Asn Ser His His Gln Asp Arg Ser His Ala Asp
                245                 250                 255

Arg Ala Ser Thr Gln His Tyr Gln Thr Gln Ala Gly Ser His Thr Gln
           260                 265                 270

Ile His Thr Gln Met Val Glu Gln Ala Trp Gly Gln Thr Gly Ser
       275                 280                 285

Asp Ser Ile Gln Thr Gln Gly Ser Ile Tyr Gln Ser Thr Glu Thr
   290                 295                 300

Val Ile His Gly Gln Asp Arg Asn Gln Ala Ser Gln Ser Val Lys Glu
305                 310                 315                 320
```

```
His His Gln Ala Gln Gly Glu Ser Tyr Ile Gln Thr His Thr Gln Thr
                325                 330                 335
Met Glu Gln Gly Arg Ser Gln Ala Glu Asn Ser Ser Thr Gln Thr
            340                 345                 350
His Gly Ser Met Tyr Gly Gln Asn Arg Glu Thr Glu Ile His Gly Leu
        355                 360                 365
Glu Ser Ser Gln Ala Glu Gln Val Gly Thr Arg His Tyr Gln Thr Gln
    370                 375                 380
Ala Gly Ser Tyr Thr Gln Thr Leu Glu His Asp Gly Ser Gln Ser Ala
385                 390                 395                 400
His Lys Phe Val Ala Gln Glu Lys Glu Arg Thr Gln Thr Lys Pro Cys
                405                 410                 415
Met Gly Gln Ser Trp Thr Pro Val Ser Asn Tyr Glu Thr Glu Glu Ser
            420                 425                 430
Val Ile Gly Gly Gln Val Gln Thr Glu Thr Asp Thr Ile Ile Glu Asn
        435                 440                 445
His Pro Ser Pro Thr Ala Arg Gln Val Glu Arg Val Pro Thr Val Val
    450                 455                 460
Arg Glu Glu Trp Val Asn Asp His Thr Arg Glu Ile Val Ile Arg Ser
465                 470                 475                 480
Gln Asp Pro Gly Ser Leu His Ser Gly Thr Pro Ser Ala Gln Gly Gln
                485                 490                 495
Asp Ile Pro Gln Met Glu Lys Lys Gly Ile Thr Ala Lys Gly Leu Tyr
            500                 505                 510
Thr Tyr Leu Lys Thr Glu Gln Pro
        515                 520

<210> SEQ ID NO 5
<211> LENGTH: 2551
<212> TYPE: DNA
<213> ORGANISM: Rattus norvegicus

<400> SEQUENCE: 5
tgatgacact taatagctac cacttagcat aagccaagca tcagctgggt gcttttatg      60 aattatctcc taaagccttt atgataccct tctgaagtaa gtgctagtat cagctccatt    120
cacagtgaag aaactgaggc atggacaagc aaagcaggta ggtggtggaa cccggcatta    180
aatgttgact cagaaatttc catggtctga gtgactctcc ttcccatcat aaagtacatt    240
ttgaggagaa gaacaaggaa ggtggagaaa cccaaacaca gctgaagaca caatgaaagg    300
accgggcctt ggcatactgt gtggaaacat caggggctga ctatggtgcc cataaaaagc    360
attttcatat tttccagcat agcttcaaag atgcctcagt tgctgcgaaa tatccatggg    420
atcatcgaag ccttcgggtg ctatgccagg tcagagggtg gctgcaaagt actcacgaag    480
caggagctga gaggcttct ggaatatgag tttgccgacg tcatagtgaa gccccatgat    540
cctgcaactg tggatgaagt tctgcacctg ttggatgaag ataacacagg aactgtagaa    600
ttcaaggaat tcttggtctt ggtgtttaaa gttgcccgtg cctgctttaa gacactgaat    660
gagagtccta agggtgcttg catgtctgac aagtctgaaa gctgccatgt tggatcttcc    720
aaagagctgg agcaaggaca gaggggtggt gctgaagtgg caaaggatgg agcagcacag    780
cactgtgaaa acagcagttg tggacagaga gatcaggctt ctagaggaca ggacagggtg    840
gggacacata cccagcatca ggacagctac cctacatggg tcagcagtca tgacaggcag    900
gctgagtctc agacacagga gatgataagc cagcaaacac aagtgacagg accagtggaa    960
```

```
cagaccccaa aaatagaaga caagagttgc atcggacaga agagatcaga gagacaacca    1020
cagatcagcc aacagacaga tgagatcaca actgaatcca caactcagac ccaagcaggc    1080
accttctaca cacagggatc tacctgtgat cagaacagag gaacaaacag ccttacccaa    1140
gacagaagtc agacagacca agcttctaca caacactacc agacacgggc agggtctcat    1200
actcagatac acaaccagac ggtggaacag ggctggggac agcagacagg aaaaaacaac    1260
atccaaatac agggatctat ctatgaccag agcagagaga ctgagattcg tggccaagat    1320
aggaaccagg caagccagac tgctaaagaa caccaccagg cacaggcaga gtcatatact    1380
cgggcgcaca ctcagacaat ggaacaaggc aggagccagc aggaagaaaa tggcagtatc    1440
cagactcatg cttccatctg tggccaaaac agaggaacca agatccatga gcaagaaagc    1500
aatcaggtag aacaggtggg aacaggacac tgccagacac aggcaggatc agatgcccag    1560
actttggagc ataatgggag ccattctgca cgacaagtag tggctcaaga aaagggacaa    1620
atgcagacac agtcatgcat ggggcaaagc tggacaccag tgagcaacta tgagacagga    1680
gagccagtgc taggacaggt ccagactgag atagacactg ttaaagaaag acaaccgtgg    1740
aacagcaatc acccaagtct ggcaggaagg cagggagaaa gaagccccac agtggttaga    1800
gaggagtggg tcaatgacca cacaagagaa atagtgatcc gaagccagga tccaggcagc    1860
ctgcactctg gtgctccttc agctcagggc caggatacag cacagatgga gaagaaagga    1920
atcacagcca agggattata ttcgtacctg aagacagagc agccatgact tctcctgact    1980
ccagtgccca taccaaaaga cagctgcagt gaggttggcc tgccttgtcc tgtgctgccc    2040
tgtcacagca cttcactgga cagctatgat tcttctcatt tggttctttt tcagcaatca    2100
tttctacaag gtgatttctt gtctaaactt acctctcttg cccggtgctc tcagaaactc    2160
acctctctta tctgctactc tcaggaacag gaagccatgg aggaggtcat ctcattgcac    2220
tgaatttctt ccaactttca ggggtttca aagctgtttt atctctgcta tcggtccatt    2280
gcatcaataa aggcttagca gctggtttca gtgtgttatt caatagtttc tactgatgtg    2340
acaaactgag agctctagag ttctgatgtt gaactgaaca tagcctcatc tctcaaggaa    2400
gactgagtta gaacgagcta aatagaggag agagcacact gtatacttgg cagagatggg    2460
tcagggatgt cttcttccat aaagatgctt atttgtagta gccctcaaaa ggacaactaa    2520
gagaaacaga gatataatta ctatcattca g                                  2551
```

<210> SEQ ID NO 6
<211> LENGTH: 541
<212> TYPE: PRT
<213> ORGANISM: Rattus norvegicus

<400> SEQUENCE: 6

Met Val Pro Ile Lys Ser Ile Phe Ile Phe Ser Ser Ile Ala Ser Lys
1               5                   10                  15

Met Pro Gln Leu Leu Arg Asn Ile His Gly Ile Ile Glu Ala Phe Gly
            20                  25                  30

Cys Tyr Ala Arg Ser Glu Gly Gly Cys Lys Val Leu Thr Lys Gln Glu
        35                  40                  45

Leu Lys Arg Leu Leu Glu Tyr Glu Phe Ala Asp Val Ile Val Lys Pro
    50                  55                  60

His Asp Pro Ala Thr Val Asp Glu Val Leu His Leu Leu Asp Glu Asp
65                  70                  75                  80

Asn Thr Gly Thr Val Glu Phe Lys Glu Phe Leu Val Leu Val Phe Lys

-continued

```
                85                  90                  95
Val Ala Arg Ala Cys Phe Lys Thr Leu Asn Glu Ser Pro Lys Gly Ala
            100                 105                 110
Cys Met Ser Asp Lys Ser Glu Ser Cys His Val Gly Ser Ser Lys Glu
            115                 120                 125
Leu Glu Gln Gly Gln Arg Gly Gly Ala Glu Val Ala Lys Asp Gly Ala
            130                 135                 140
Ala Gln His Cys Glu Asn Ser Ser Cys Gly Gln Arg Asp Gln Ala Ser
145                 150                 155                 160
Arg Gly Gln Asp Arg Val Gly Thr His Thr Gln His Gln Asp Ser Tyr
                165                 170                 175
Pro Thr Trp Val Ser Ser His Asp Arg Gln Ala Glu Ser Gln Thr Gln
            180                 185                 190
Glu Met Ile Ser Gln Gln Thr Gln Val Thr Gly Pro Val Glu Gln Thr
            195                 200                 205
Pro Lys Ile Glu Asp Lys Ser Cys Ile Gly Gln Lys Arg Ser Glu Arg
            210                 215                 220
Gln Pro Gln Ile Ser Gln Gln Thr Asp Glu Ile Thr Thr Glu Ser Thr
225                 230                 235                 240
Thr Gln Thr Gln Ala Gly Thr Phe Tyr Thr Gln Gly Ser Thr Cys Asp
                245                 250                 255
Gln Asn Arg Gly Thr Asn Ser Leu Thr Gln Asp Arg Ser Gln Thr Asp
            260                 265                 270
Gln Ala Ser Thr Gln His Tyr Gln Thr Arg Ala Gly Ser His Thr Gln
            275                 280                 285
Ile His Asn Gln Thr Val Glu Gln Gly Trp Gly Gln Thr Gly Lys
            290                 295                 300
Asn Asn Ile Gln Ile Gln Gly Ser Ile Tyr Asp Gln Ser Arg Glu Thr
305                 310                 315                 320
Glu Ile Arg Gly Gln Asp Arg Asn Gln Ala Ser Gln Thr Ala Lys Glu
                325                 330                 335
His His Gln Ala Gln Ala Glu Ser Tyr Thr Arg Ala His Thr Gln Thr
            340                 345                 350
Met Glu Gln Gly Arg Ser Gln Glu Glu Asn Gly Ser Ile Gln Thr
            355                 360                 365
His Ala Ser Ile Cys Gly Gln Asn Arg Gly Thr Lys Ile His Glu Gln
            370                 375                 380
Glu Ser Asn Gln Val Glu Gln Val Gly Thr Gly His Cys Gln Thr Gln
385                 390                 395                 400
Ala Gly Ser Asp Ala Gln Thr Leu Glu His Asn Gly Ser His Ser Ala
                405                 410                 415
Arg Gln Val Val Ala Gln Glu Lys Gly Gln Met Gln Thr Gln Ser Cys
            420                 425                 430
Met Gly Gln Ser Trp Thr Pro Val Ser Asn Tyr Glu Thr Gly Glu Pro
            435                 440                 445
Val Leu Gly Gln Val Gln Thr Glu Ile Asp Thr Val Lys Glu Arg Gln
            450                 455                 460
Pro Trp Asn Ser Asn His Pro Ser Leu Ala Gly Arg Gln Gly Glu Arg
465                 470                 475                 480
Ser Pro Thr Val Val Arg Glu Glu Trp Val Asn Asp His Thr Arg Glu
                485                 490                 495
Ile Val Ile Arg Ser Gln Asp Pro Gly Ser Leu His Ser Gly Ala Pro
            500                 505                 510
```

```
Ser Ala Gln Gly Gln Asp Thr Ala Gln Met Glu Lys Lys Gly Ile Thr
        515                 520                 525

Ala Lys Gly Leu Tyr Ser Tyr Leu Lys Thr Glu Gln Pro
530                 535                 540
```

*CRNN* LOSS OF FUNCTION RODENT MODEL

CROSS REFERENCE TO RELATED APPLICATION

This application claims the benefit of priority from U.S. Provisional Application No. 62/909,982, filed Oct. 3, 2019, the entire contents of which are incorporated herein by reference.

FIELD OF THE DISCLOSURE

This disclosure relates to a genetically modified rodent and use thereof as a rodent model. More specifically, this disclosure relates to rodent (e.g., mouse or rat) comprising a loss of function mutation in an endogenous Crnn (cornulin) gene, and to use of such a rodent animal as a rodent model of skin inflammation disorders (e.g., psoriasis).

INCORPORATION BY REFERENCE OF SEQUENCE LISTING

The sequence listing in the ASCII text file, named as 37187_10546US01_SequenceListing of 22 KB, created on Oct. 1, 2020, and submitted to the United States Patent and Trademark Office via EFS-Web, is incorporated herein by reference.

BACKGROUND

Various references, including patents, patent applications, accession numbers, technical articles, and scholarly articles are cited throughout the specification. Each reference is incorporated by reference herein, in its entirety and for all purposes.

Psoriasis is an inflammatory disease of the skin characterized by thickening and the appearance of red plaques or dry scales in the skin. Animal models of psoriasis are important to the understanding of the mechanisms underlying the disease, as well as to identification and evaluation of new and effective treatment of the disease.

SUMMARY OF THE DISCLOSURE

Disclosed herein are rodents (e.g., mice and rats) whose genome comprises a loss of function mutation in an endogenous Crnn gene, and isolated rodent cells (e.g., ES cells) or tissues comprising a loss of function mutation in an endogenous Crnn gene. Also disclosed herein are compositions (e.g., targeting vectors) and methods for the production of the rodents whose genome comprises a loss of function mutation in an endogenous Crnn gene. Further disclosed herein are methods of using the rodents as an animal model of skin inflammation disorders (e.g., psoriasis).

In one aspect, disclosed herein is a rodent whose genome comprises a loss of function mutation in an endogenous Crnn gene at an endogenous rodent Crnn locus. A loss of function mutation in an endogenous Crnn gene at an endogenous rodent Crnn locus results in the lack of a functional Crnn polypeptide being expressed from the Crnn locus.

In some embodiments, a loss of function mutation comprises a deletion, in whole or in part, of the coding sequence of an endogenous rodent Crnn gene. In some embodiments, the deletion comprises exon 2 in whole or in part, and/or exon 3 in whole or in part, of an endogenous rodent Crnn gene. In some embodiments, the deletion comprises a nucleic acid sequence from the nucleotide after the ATG start codon in exon 2 through the stop codon of an endogenous rodent Crnn gene.

In some embodiments, the rodent Crnn locus which comprises a loss of function mutation in an endogenous Crnn gene further comprises a reporter gene.

In some embodiments, the reporter gene is operably linked to the endogenous Crnn promoter at the Crnn locus. In specific embodiments, the Crnn locus comprises a deletion beginning from the nucleotide after the ATG start codon in exon 2 through the stop codon of the endogenous rodent Crnn gene, and comprises a reporter gene coding sequence that is fused in-frame to the start (ATG) codon of the Crnn locus.

In some embodiments, the reporter gene is lacZ. In some embodiments, the reporter gene is selected the group consisting of luciferase, green fluorescent protein (GFP), enhanced GFP (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, and MmGFP.

In some embodiments, a rodent is homozygous for a loss of function mutation in an endogenous Crnn gene. In some embodiments, a rodent is heterozygous for a loss of function mutation in an endogenous Crnn gene.

In some embodiments, a rodent is a mouse. In some embodiments, a rodent is a rat.

Also provided herein is a progeny of any of the rodents disclosed herein.

In a further aspect, disclosed herein is an isolated rodent cell or tissue whose genome comprises a loss of function mutation in an endogenous rodent Crnn gene at an endogenous rodent Crnn locus.

In some embodiments, the isolated rodent cell is a rodent embryonic stem cell, or a rodent egg.

In another aspect, disclosed herein is a rodent embryo whose genome comprises a loss of function mutation in an endogenous rodent Crnn gene at an endogenous rodent Crnn locus.

In still a further aspect, disclosed herein is a method of making a rodent whose genome comprises a loss of function mutation in an endogenous rodent Crnn gene at an endogenous rodent Crnn locus. The method comprises modifying a rodent genome such that the modified rodent genome comprises a loss of function mutation in an endogenous rodent Crnn gene at an endogenous rodent Crnn locus, and obtaining a rodent comprising the modified genome.

In some embodiments, a rodent genome is modified by introducing a nucleic acid molecule into a rodent embryonic stem cell, which nucleic acid molecule comprises an insert nucleotide sequence to be integrated into the endogenous rodent Crnn locus, flanked by polynucleotide sequences that are homologous to nucleic acid sequences at the endogenous rodent Crnn locus. Integration of the insert nucleotide sequence results in a loss of function mutation in an endogenous rodent Crnn gene at the Crnn locus. The resulting genetically modified rodent embryonic stem cell is then used to make a rodent.

In some embodiments, a loss of function mutation comprises a deletion, in whole or in part, of the coding sequence of an endogenous rodent Crnn gene. In some embodiments, the deletion comprises a nucleic acid sequence from the nucleotide after the ATG start codon in exon 2 through the stop codon of an endogenous rodent Crnn gene.

In some embodiments, a rodent made by the present method further comprises a reporter gene. For example, a reporter gene can be included in the nucleic acid sequence being introduced into the genome of a rodent embryonic stem cell. In some embodiments, the reporter gene is operably linked to the endogenous Crnn promoter at the Crnn locus in the modified genome. In specific embodiments, the Crnn locus of a modified genome comprises a deletion beginning from the nucleotide after the ATG start codon in exon through the stop codon in exon 3 of the endogenous rodent Crnn gene, and comprises a reporter gene coding sequence that is fused in-frame to the start (ATG) codon of the Crnn locus.

In some embodiments, the reporter gene is lacZ. In some embodiments, the reporter gene is selected the group consisting of luciferase, green fluorescent protein (GFP), enhanced GFP (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, and MmGFP.

In some embodiments, a rodent made by the present method further comprises a selection marker. For example, a selection marker gene can be included in the nucleic acid sequence being introduced into the genome of a rodent embryonic stem cell. In some embodiments, the nucleic acid sequence may further comprise site-specific recombinase recognition sites flanking the selection marker gene, which site-specific recombinase recognition sites are oriented to direct an excision of the selection marker by a recombinase.

In some embodiments, a rodent made by the present method is heterozygous for a loss of function mutation in an endogenous Crnn gene. Rodents heterozygous for a loss of function mutation in an endogenous Crnn gene can be bred with each other to obtain rodents homozygous for the loss of function mutation in an endogenous Crnn gene.

In some embodiments, a rodent made by the present method is a mouse. In some embodiments, a rodent made by the present method is a rat.

In a further aspect, disclosed herein is a targeting nucleic acid construct, comprising a nucleotide sequence to be integrated into a rodent Crnn locus, flanked by a 5' nucleotide sequence and a 3' nucleotide sequence that are homologous to nucleotide sequences at the rodent Crnn locus, wherein integration of the nucleotide sequence into the rodent Crnn locus results in a loss of function mutation in the endogenous rodent Crnn gene as described herein. The targeting nucleic acid construct can be designed so as to be capable of integrating the n nucleotide sequence into a mouse or rat Crnn gene at an endogenous mouse or rat Crnn locus. In some embodiments, the nucleotide sequence to be integrated into a rodent Crnn gene at an endogenous rodent Crnn locus includes a reporter gene. In some embodiments, the nucleotide sequence to be integrated into a rodent Crnn gene at an endogenous rodent Crnn locus includes a selectable marker gene.

In a further aspect, disclosed herein is a method of breeding, comprising breeding a first rodent whose genome comprises a loss of function mutation in an endogenous rodent Crnn gene, with a second rodent, resulting in a progeny rodent whose genome comprises the loss of function mutation in an endogenous rodent Crnn gene.

In a further aspect, disclosed herein is use of a rodent whose genome comprises a loss of function mutation in an endogenous Crnn gene as an animal model for human disorders such as skin inflammation (e.g., psoriasis). Such animal model permits elucidation of the mechanisms of skin disorders, as well as the role of Crnn action in the context of skin disorders, and provides opportunities to test and develop therapeutics to treat disorders such as skin inflammation. In some embodiments, a rodent model of skin inflammation diseases comprises a rodent disclosed herein, to which a skin inflammation inducing agent is applied. In some embodiments, skin inflammation is induced by imiquimod (IMQ).

In some embodiments, a rodent disclosed herein displays enhanced inflammation in an experimentally induced skin inflammation model as compared to a wild type rodent.

In still a further aspect, disclosed herein is a method of assessing the therapeutic efficacy of a candidate compound for treating such as skin inflammation (e.g., psoriasis), comprising administering an agent to a rodent disclosed herein to induce skin inflammation, administering a candidate compound to the rodent, and determining whether the candidate compound inhibits and/or reduces induced skin inflammation.

In some embodiments, the agent administered to induce skin inflammation is IMQ.

In some embodiments, a candidate compound is administered to the rodent before, during, or after the administration of an agent that induces inflammation. In some embodiments, a candidate compound can be a small molecule compound, a nucleic acid inhibitor, or an antigen-binding protein such as an antibody.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION

Figure 1:
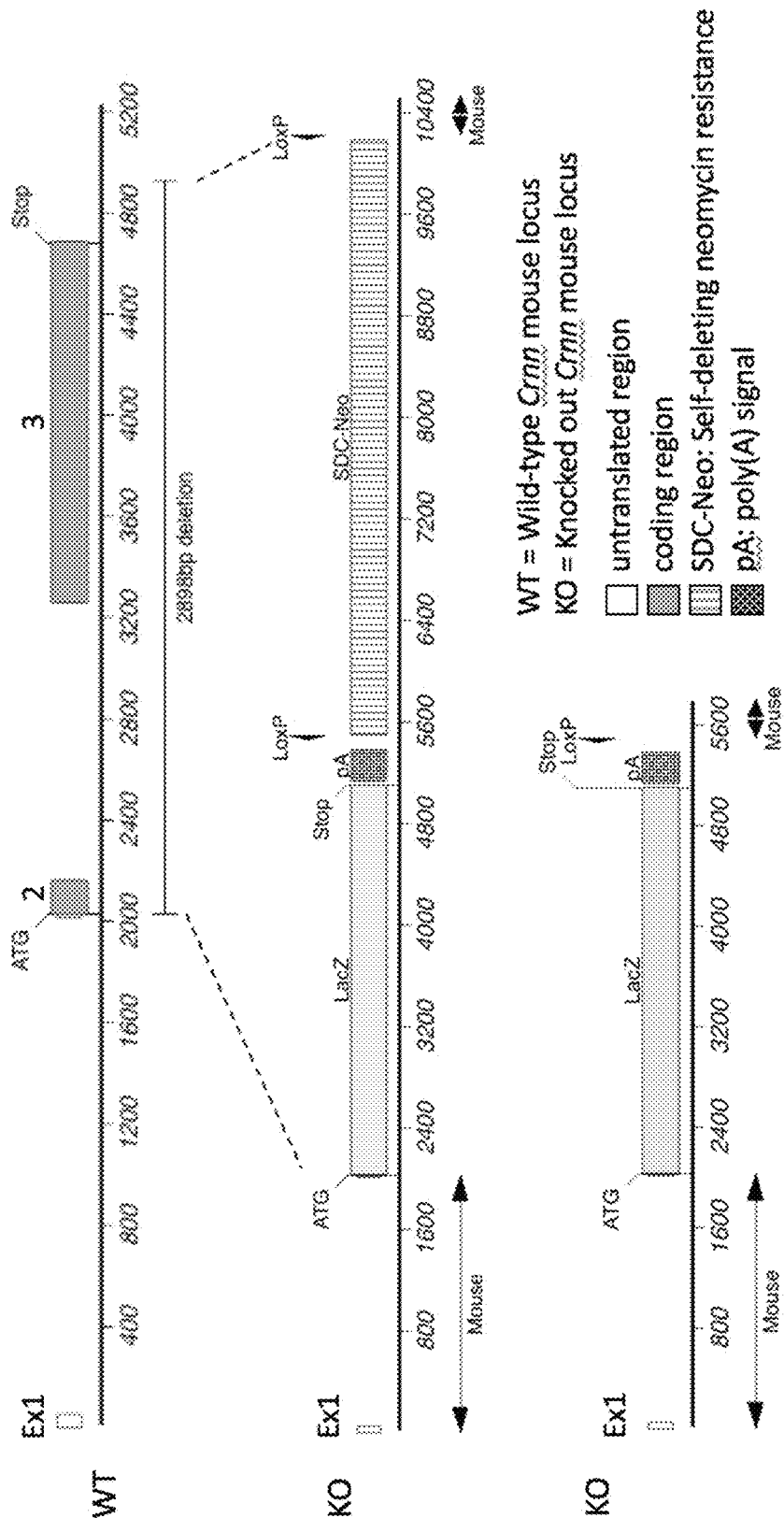
FIG. 1 depicts an exemplary targeting strategy for ablation of the Crnn gene and generation of a Crnn knock-out (Crnn$^{-/-}$) mouse.

Disclosed herein are genetically modified rodent animals that carry a loss of function mutation in an endogenous rodent Crnn gene (such as Crnn knock-out mice, also referred to as "Crnn KO" or "Crnn$^{-/-}$" mice, and Crnn$^{+/-}$ mice), and use of such animals as an animal model of skin inflammation disorders such as psoriasis. Phenotyping of the Crnn KO mice shows strong expression of a reporter gene in the epidermis consistent with the known function of Crnn as a member of the epidermal differentiation complex (EDC). Additionally, using an imiquimod (IMQ)-induced model of psoriasis, the Crnn$^{-/-}$ and Crnn$^{+/-}$ mice have been shown to be more susceptible to the IMQ treatment as compared to wild type mice. The IMQ-treated Crnn$^{-/-}$ and Crnn$^{+/-}$ mice showed increased skin thickness and inflammation and elevation of pro-inflammatory cytokines versus IMQ-treated wild-type mice. The data on the phenotypic characterization of the Crnn loss of function mouse model supports the notion that deficiency of Cornulin in the epidermis increases the susceptibility to developing psoriasis.

CRNN

CRNN (Cornulin) is a member of the epidermal differentiation complex (EDC). It contains two EF-hand Ca2+ binding domains in its N-terminus and two glutamine- and threonine-rich 60 amino acid repeats in its C-terminus. EDC proteins are crucial for development, maintenance and maturation of the epidermis.

The protein structure and the genomic structure of Cornulin are conserved across species. Exemplary wild type Crnn mRNA and protein sequences from human, mouse and rat are available in GenBank under the following accession numbers, and are also set forth as SEQ ID NOS: 1-6 in the Sequence Listing.

TABLE 1

| SEQ ID | Description | Features |
|---|---|---|
| 1 | Homo sapiens CRNN mRNA NM_016190.3 | Length: 1902 bp Exons: 1 . . . 50, 51 . . . 201, 202 . . . 1902 CDS: 64-1551 |
| 2 | Homo sapiens CRNN protein, NP_05274.1 | Length: 495 aa S-100 domain: 2-89; Ca2+ binding site: 19, 24, 27, 32-33, 62, 64, 66, 68, 70, 73; EF-hand domain: 28-75 |
| 3 | Mus musculus Crnn mRNA, NM_001081200.2 | Length: 1973 bp Exons: 1 . . . 50, 51 . . . 201, 202 . . . 1973 CDS: 64-1626 |
| 4 | Mus musculus Crnn protein, NP_001074669.1 | Length: 520 aa S-100 domain: 2-89; Ca2+ binding site: 19, 24, 27, 32-33, 62 64, 66, 68, 70, 73; EF-hand domain: 28-75 |
| 5 | Rattus norvegicus Crnn predicted transcript variant X1 mRNA XM_227367.6 | Length: 2551 bp CDS: 343-1968 |
| 6 | Rattus norvegicus Crnn protein XP_227367.5 | Length: 541 aa S-100 domain: 18-105; Ca2+ binding site: 35, 40, 43, 48 . . . 49, 78, 80, 82, 84, 86, 89 |

Rodents Comprising a Loss of Function Mutation in an Endogenous Crnn Gene

Disclosed herein are rodents (e.g., mice and rats) whose genome comprises a loss of function mutation in the endogenous Crnn gene.

The term "mutation" includes an addition, deletion, or substitution of one or more nucleotides in a gene (e.g., a wild type Crnn allele). In some embodiments, a mutation is a substitution of a single nucleotide. In other embodiments, a mutation is a deletion of one or more nucleotides, e.g., one or more nucleotides in the coding sequence of a gene. In some embodiments, a loss of function mutation in a gene includes a deletion of a contiguous nucleic acid sequence, e.g., one or more exons, in full or in part, of a gene.

In some embodiments, a mutation in a gene results in an addition, deletion, or substitution of one or more amino acids in the encoded protein (e.g., a wild type Crnn protein).

In some embodiments, a mutation in a gene results in a lack of functional protein being expressed or produced— such a mutation is also referred to herein as a "loss of function" mutation. In some embodiments, a loss of function mutation in a gene causes a deletion of one or more amino acids, resulting in a mutant protein that lacks the function of the wild type protein. In some embodiments, a loss of function mutation in a gene includes a deletion of a contiguous nucleic acid sequence, e.g., one or more exons in full or in part, resulting in a lack of expression of a protein from the mutant gene or resulting in an expression of a protein that lacks the function of the wild type protein.

In some embodiments, a loss of function mutation in a Crnn gene includes a deletion of the first coding exon (i.e., exon 2) in whole or in part, e.g., the coding portion of exon 2 beginning from the nucleotide after the ATG codon. In some embodiments, a loss of function mutation in a Crnn gene includes a deletion of the second coding exon (i.e., exon 3) in whole or in part. In some embodiments, a loss of function mutation in a Crnn gene includes a deletion of a nucleotide sequence coding for a peptide portion that comprises an EF-hand domain, or amino acids involved in Ca$^{2+}$ binding, and/or the S-100 domain. In some embodiments, a loss of function mutation in a Crnn gene includes a deletion of the coding sequence of exon 2 beginning from the nucleotide after the ATG codon and a deletion of exon 3 at least through the stop codon. In some embodiments, a loss of function mutation in a Crnn gene includes a deletion of the coding sequence of exon 2 beginning from the nucleotide after the ATG codon and a deletion of entire exon 3 (i.e., through the stop codon and the 3' untranslated region).

In some embodiments, a rodent whose genome comprises a loss of function mutation in an endogenous Crnn gene further comprises an insertion of a reporter gene, and wherein the reporter gene is operably linked to the endogenous rodent Crnn promoter at the endogenous rodent Crnn locus.

In some embodiments, a genomic fragment beginning from the nucleotide after the start codon in exon 2 through the whole or part of exon 3 of an endogenous Crnn gene has been deleted, and the reporter gene is inserted immediately downstream of the start codon of the endogenous rodent Crnn gene. In such linkage, expression of the reporter gene is expected to resemble the expression pattern of an unmodified endogenous rodent Crnn gene.

Multiple reporter genes are known in the art and are suitable for use herein. In some embodiments, the reporter gene is a LacZ gene. In some embodiments, the reporter gene is a gene encoding a protein selected the group consisting of luciferase, green fluorescent protein (GFP), enhanced GFP (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, and MmGFP.

For any of the embodiments described herein, the rodents can include, for example, mice, rats, and hamsters.

In some embodiments, the rodent is a mouse. In some embodiments, the rodent is a mouse of a C57BL strain, for example, a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In other embodiments, the rodent is a mouse of a 129 strain, for example, a 129 strain selected from the group consisting of 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al. (1999), *Mammalian Genome* 10:836; Auerbach et al. (2000), *Biotechniques* 29(5):1024-1028, 1030, 1032). In some embodiments, the rodent is a mouse that is a mix of an aforementioned 129 strain and an aforementioned C57BL/6 strain. In certain embodiments, the mouse is a mix (i.e., hybrid) of aforementioned 129 strains, or a mix of aforementioned C57BL strains, or a mix of a C57BL strain and a 129 strain. In certain embodiments, the mouse is a mix of a C57BL/6 strain with a 129 strain. In specific embodiments, the mouse is a VGF1 strain, also known as F1H4, which is a hybrid of C57BL/6 and 129. In other embodiments, the mouse is a BALB strain, e.g., BALB/c strain. In some embodiments, the mouse is a mix of a BALB strain and another aforementioned strain.

In some embodiments, the rodent is a rat. In certain embodiments, the rat is selected from a Wistar rat, an LEA strain, a Sprague Dawley strain, a Fischer strain, F344, F6, and Dark Agouti. In other embodiments, the rat is a mix of two or more strains selected from the group consisting of Wistar, LEA, Sprague Dawley, Fischer, F344, F6, and Dark Agouti.

In some embodiments, a genetically modified rodent having a loss of function mutation in the endogenous Crnn gene is more susceptible to an imiquimod (IMQ) treatment (e.g., by displaying increased inflammation) as compared to a wild type rodent in an IMQ-induced model of psoriasis. In some embodiments, IMQ is applied topically to the skin of a rodent to induce skin inflammation. In some embodiments, IMQ is provided in a carrier suitable for topical application, e.g., a cream, a gel, including commercially available IMQ creams (e.g., such as those from Aldara). In some embodiments, to induce skin inflammation, IMQ is applied to the rodent skin daily at a daily dose of 1 to 5 mg, 2 to 4 mg, or 3 to 3.5 mg, for a period of 3 to 5 days, e.g., for 4 days. In some embodiments, a daily topical application at a daily dosage of about 3.125 mg for 4 days is suitable for inducing acute skin inflammation.

In some embodiments, the severity of the skin inflammation can be evaluated by (i) using an adapted version of the clinical Psoriasis Area and Severity Index based on measuring and independently scoring erythema, scaling and thickening of the skin; (ii) performing histopathological analysis of skin tissues, e.g., to evaluate and score each of the following parameters: hyperkeratosis, parakeratosis, Munro's microabscess (accumulation of neutrophils in the stratum corneum), acanthosis, epidermal erosion or ulceration, inflammation (inflammatory cell infiltrates) in the dermis and hypodermis, blood vessel congestion in the dermis and hypodermis, and to determine a total pathology score; (iii) measuring concentrations of proinflammatory cytokines in the skin homogenates, including e.g., concentrations of myeloperoxidase, KC-GRO, IL-6, IL-1β, TNFα, IL-36 ligands such as IL-36α and IL-36β, among others; and (iv) a combination of (i)-(iii).

In some embodiments, a genetically modified rodent having a loss of function mutation in an endogenous Crnn gene displays increased skin inflammation after an IMQ treatment as compared to wild-type mice based on visual scoring, individual scoring or total scoring, of erythema, scaling and thickening. In some embodiments, a genetically modified rodent having a loss of function mutation in an endogenous Crnn gene displays increased skin inflammation after an IMQ treatment as compared to wild-type mice based on measured skin thickness.

In some embodiments, a genetically modified rodent having a loss of function mutation in an endogenous Crnn gene displays increased skin inflammation after an IMQ treatment as compared to wild-type mice based on an increased total score from evaluating and scoring each of the following parameters: hyperkeratosis, parakeratosis, Munro's microabscess (accumulation of neutrophils in the stratum corneum), acanthosis, epidermal erosion or ulceration, inflammation (inflammatory cell infiltrates) in the dermis and hypodermis, blood vessel congestion in the dermis and hypodermis.

In some embodiments, a genetically modified rodent having a loss of function mutation in an endogenous Crnn gene displays increased skin inflammation after an IMQ treatment as compared to wild-type mice based on elevated levels of pro-inflammatory cytokines (e.g., one or more of myeloperoxidase, KC-GRO, IL-6, IL-1β, TNFα, IL-36 ligands such as IL-36α and IL-36β) in skin homogenates by at least 20%, 30%, 40%, 50%, 60%, 70%, 80%, 90%, 100%, or more.

In some embodiments, a genetically modified rodent having a loss of function mutation in an endogenous Crnn gene displays an increased trans-epidermal water vapor loss (TEWL) after an IMQ treatment as compared to wild-type mice, e.g., an increase by at least 20%, 30%, 40%, 50%, 60%, 70%, 80%, 90%, 100%, or more.

Also disclosed herein are isolated rodent cells or tissues whose genome comprises a loss of function mutation in an endogenous Crnn gene, described herein. In some embodiments, an isolate rodent cell is an embryonic stem (ES) cell. Rodent embryos and eggs comprising a loss of function mutation in an endogenous Crnn gene are also provided.

Methods of Making a Rodent, Methods of Breeding, and Targeting Vectors

Disclosed herein are methods for the production of the rodents having a loss of function mutation in an endogenous Crnn gene.

In some embodiments, the method comprises modifying a rodent genome such that the modified rodent genome comprises a loss of function mutation in an endogenous rodent Crnn gene at an endogenous rodent Crnn locus, and obtaining a rodent comprising the modified genome.

In some embodiments, a rodent genome is modified by, e.g., employing a zinc finger nuclease (ZFN), a transcription activator-like effector nuclease (TALEN), or a Cas protein (i.e., a. CRISPR/Cas system), such that the modified genome includes a loss of function mutation in an endogenous rodent Crnn gene at an endogenous rodent Crnn locus.

In some embodiments, a rodent genome is modified by introducing a nucleic acid molecule into a rodent embryonic stem (ES) cell, wherein the nucleic acid molecule comprises a nucleotide sequence desired to be integrated into the Crnn locus (i.e., an insert nucleotide sequence) to create a loss of function mutation in an endogenous rodent Crnn gene. The insert nucleotide sequence is flanked by polynucleotide sequences that are homologous to nucleic acid sequences at the endogenous rodent Crnn locus and capable of mediating homologous recombination of the insert nucleotide sequence into the genome of the ES cell, such that the modified genome comprises a loss of function mutation in an endogenous rodent Crnn gene at the endogenous rodent Crnn locus. The resulting genetically modified rodent embryonic stem cell can then be used in making a genetically modified rodent.

In some embodiments, the insert nucleotide sequence to be integrated into the genome of a rodent ES cell is provided in a targeting nucleic acid construct (i.e., a targeting vector), preferably a DNA vector. In some embodiments, the insert nucleotide sequence also contains a selectable marker gene (e.g., a self deleting cassette containing a selectable marker gene, as described in U.S. Pat. Nos. 8,697,851, 8,518,392 and 8,354,389, all of which are incorporated herein by reference), which can be flanked by or comprises site-specific recombination sites (e.g., loxP, Frt, etc.). The selectable marker gene can be placed on the vector adjacent to the mutation to permit easy selection of transfectants. In some embodiments, the insert nucleotide sequence also contains a reporter gene.

In some embodiments, a targeting vector (e.g., a BAC vector) can be introduced into rodent embryonic stem (ES) cells by, e.g., electroporation. Both mouse ES cells and rat ES cells have been described in the art. See, e.g., U.S. Pat. Nos. 7,576,259, 7,659,442, 7,294,754, and US 2008-0078000 A1 (all of which are incorporated herein by reference) describe mouse ES cells and the VELOCIMOUSE® method for making a genetically modified mouse; and US 2014/0235933 A1 and US 2014/0310828 A1 (all of which are incorporated herein by reference) describe rat ES cells and methods for making a genetically modified rat.

Homologous recombination in recipient cells can be facilitated by introducing a break in the chromosomal DNA at the integration site, which may be accomplished by targeting certain nucleases to the specific site of integration. DNA-binding proteins that recognize DNA sequences at the target locus are known in the art. In some embodiments, zinc finger nucleases (ZFNs), which recognize a particular 3-nucleotide sequence in a target sequence, are utilized. In some embodiments, Transcription activator-like (TAL) effector nucleases (TALENs) are employed for site-specific genome editing. In other embodiments, RNA-guided endonucleases (RGENs), which consist of components (Cas9 and tracrRNA) and a target-specific CRISPR RNA (crRNA), are utilized.

In some embodiments, a targeting vector carrying a nucleic acid of interest (e.g., an insert nucleotide sequence for generating a loss of function Crnn mutant gene), flanked by 5' and 3' homology arms, is introduced into a cell with one or more additional vectors or mRNA. In one embodiment, the one or more additional vectors or mRNA contain a nucleotide sequence encoding a site-specific nuclease, including but not limited to a zinc finger nuclease (ZFN), a ZFN dimer, a transcription activator-like effector nuclease (TALEN), a TAL effector domain fusion protein, and an RNA-guided DNA endonuclease.

ES cells having an insert nucleotide sequence integrated in the genome can be selected. After selection, positive ES clones can be modified, e.g., to remove a self-deleting cassette, if desired. ES cells having the mutation integrated in the genome can then be used as donor ES cells for injection into a pre-morula stage embryo (e.g., 8-cell stage embryo) by using the VELOCIMOUSE® method (see, e.g., U.S. Pat. Nos. 7,576,259, 7,659,442, 7,294,754, and US 2008/0078000 A1), or methods described in US 2014/0235933 A1 and US 2014/0310828 A1. The embryo comprising the donor ES cells is incubated until blastocyst stage and then implanted into a surrogate mother to produce an F0 rodent fully derived from the donor ES cells. Rodent pups bearing the mutant allele can be identified by genotyping of DNA isolated from tail snips using a modification of allele (MOA) assay (Valenzuela et al., supra) that detects the presence of the mutant sequence or a selectable marker gene.

Further provided herein are methods of breeding a genetically modified rodent as described herein with another rodent, as well as progenies obtained from such breeding.

In some embodiments, a method is provided which comprises breeding a first genetically modified rodent as described hereinabove (e.g., a rodent whose genome comprises a loss of function Crnn mutation at an endogenous rodent Crnn locus), with a second rodent, resulting in a progeny rodent whose genome comprises the loss of function Crnn mutation. The progeny may possess other desirable phenotypes or genetic modifications inherited from the second rodent used in the breeding. In some embodiments, the progeny rodent is heterozygous for the loss of function Crnn mutation. In some embodiments, the progeny rodent is homozygous for the loss of function Crnn mutation.

In some embodiments, a progeny rodent is provided whose genome comprises a loss of function Crnn mutation at an endogenous rodent Crnn locus, wherein the progeny rodent is produced by a method comprising breeding a first genetically modified rodent as described hereinabove (e.g., a rodent whose genome comprises a loss of function Crnn mutation at an endogenous rodent Crnn locus), with a second rodent. In some embodiments, the progeny rodent is heterozygous for the loss of function Crnn mutation. In some embodiments, the progeny rodent is homozygous for the a loss of function Crnn mutation.

Rodent Model and Use Thereof

In a further aspect, disclosed herein is use of a rodent whose genome comprises a loss of function mutation in an endogenous Crnn gene as an animal model of diseases, including skin inflammation disorders such as psoriasis. Such model is useful for understanding skin inflammation biology and processes, as well as testing, screening, or identifying an agent that treats skin inflammation.

In some embodiments, disclosed here are methods for testing, screening, or identifying an agent useful for treating skin inflammation.

In some embodiments, compounds that can be evaluated using the rodents disclosed include, for example, small molecule compounds, nucleic acid-based compounds (e.g., siRNA, ribozyme, antisense construct, etc.), and an antigen-binding protein (e.g., antibody or antigen-binding fragment thereof).

Candidate compounds can be evaluated by inducing skin inflammation, e.g., by topical application of IMQ, in a rodent disclosed herein, and determining whether a candidate compound can treat or inhibit the induced inflammation. The term "treating" or "inhibiting" includes ameliorating the severity, slowing down the progression, eliminating, delaying or preventing the onset of the induced inflammation and symptoms, or a combination thereof.

In some embodiments, a rodent is administered with a candidate compound prior to, during, together with, or after administration of an agent (e.g., IMQ) that induces skin inflammation. Candidate compounds may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebro ventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. In specific embodiments, a candidate compound is administered subcutaneously at or near the skin area where an agent (e.g., IMQ) that induces skin inflammation is applied.

A compound is considered to be effective if it inhibits skin inflammation as compared to appropriate control rodents. In some embodiments, suitable control rodents can include, e.g., genetically modified rodents comprising the same loss of function mutation but without being subjected to an induced inflammation treatment; genetically modified rodents comprising the same loss of function mutation which have been subjected to an induced inflammation treatment without any candidate compound or with a control compound not expected to have any therapeutic efficacy; and genetically modified rodents comprising the same loss of function mutation which have been subjected to an induced inflammation treatment and a compound known to be therapeutically effective.

The present description is further illustrated by the following examples, which should not be construed as limiting in any way. The contents of all cited references (including literature references, issued patents, and published patent applications as cited throughout this application) are hereby expressly incorporated by reference.

EXAMPLES

Example 1, Generation of Crnn$^{-/-}$ Mice

A genetically engineered Crnn$^{-/-}$ mouse strain was created using Regeneron's VelociGene® technology (Valenzuela et al., Nat Biotechnol 2003 June; 21:652-59; Poueymirou et al., *Nat Biotechnol.* 2007 January; 25(1): 91-9; both of which are herein incorporated by reference in their entireties). Briefly, C57BL/6NTac embryonic stem cells (ESC) were targeted for ablation of a portion of the Crnn locus, beginning just after the start ATG and ending 241 base pairs beyond the stop codon. A LacZ reporter module was inserted in frame with the Crnn start, followed by a fLoxed neomycin resistance cassette for selection of correctly targeted ESCs. See FIG. 1. Correctly targeted ESCs were microinjected into 8-cell embryos from Charles River Laboratories Swiss Webster albino mice, yielding F0 VelociMice® that were 100% derived from the targeted cells (Poueymirou et al. 2007, supra). These mice were subsequently bred to homozygosity and maintained in the Regeneron animal facility during the study period. The resistance cassette was removed in the F0 germline using self-deleting technology, leaving a single loxP. Crnn$^{-/+}$ heterozygous mice and C57Bl/6NTac wild-type littermates were also included in various analysis.

Example 2, LacZ Expression in Crnn$^{-/-}$ Mice

Six to 8-week old mice were deeply anesthetized via. Ketamine/Xylazine (120/5 mg/kg) IP injection and fixed by cardiac perfusion using a 0.2% glutaraldehyde, 4% paraformaldehyde solution. Skin tissues from the head, back and ears were dissected, rinsed in PBS and post-fixed for 30 minutes in a 0.2% glutaraldehyde, 4% paraformaldehyde solution. Tissues were then washed and incubated in X-gal (1 mg/mL) staining solution for 1 to 24 hours at 37° C. After staining, tissues were rinsed in wash buffer, post-fixed in 4% paraformaldehyde, cleared in a series of 50%, 70% and 100% glycerol and imaged using an Aperio Scanscope.

Targeted, cassette-deleted heterozygous mice were bred to obtain desired genotypes. Mice that were homozygous knockout (Crnn−/−) or heterozygous knockout (Crnn+/−) for Crnn were born in expected Mendelian ratios, had normal body weight, survived to adulthood, and displayed no overt abnormalities. To determine the expression pattern of Crnn in adult mouse skin, biopsies back and ear skin from 6-8 week-old Crnn−/− mice containing two copies of the Crnn-LacZ allele were obtained, fixed, and incubated with X-gal. This LacZ reporter assay revealed very robust expression of Crnn in the epidermis and hair follicles, consistent with its known and reported role in epidermal differentiation Example 3, Crnn$^{-/-}$ Mice Displayed Increased IMQ-Induced Skin Inflammation Induction of Acute IMQ-Induced Inflammation To induce acute skin inflammation, 8 months old Crnn KO (Crnn$^{-/-}$), Crnn+/− and WT female mice had their back hair shaved using hair trimmer (Oster, MiniMax, Cat #78049-100) and skin depilated with 0.5 g Veet hair removal gel three days prior to IMQ cream application. A daily topical dose of 62.5 mg of commercially available IMQ cream (5%) (Aldara, GM Health Care Limited, NDC 99207-206-12, lot #QJ044A) or Vaseline (CVS Pharmacy, NDC 59779-902-88) was applied on the shaved back skin of the Crnn KO (n=6) and WT (n=5) mice for four consecutive days for the induction of acute disease. A daily topical dose of 62.5 mg of Aldara translated into a daily dose of 3.125 mg of an active compound. Two or three days after the treatments, the back skin of mice started to display signs of erythema, scaling and thickening. The severity of inflammation was measured on a daily basis using an adapted version of the clinical Psoriasis Area and Severity Index. Erythema, scaling and thickening were scored independently on a scale from 0-3: 0, none; 1, slight; 2, moderate; 3, marked (van der Fits L, et al., *The Journal of Immunology*, 2009; 182:5836-5845). Skin thickness was measured using caliper on d5 (Kaefer).

Trans-Epidermal Water Loss (TEWL)

Measurement of skin water vapor loss, TEWL, was used to evaluate the integrity of the dermal tissue barrier. TEWL measurements were made using the VapoMeter® device (Delfin Techonologies). Mice were anesthetized in an isoflurane inhalation chamber (3% isofluorane for 80 seconds) before the VapoMeter® (equipped with its small adaptor) was applied to the back skin of the mice to take the reading. Baseline readings were taken on the first day of treatment, prior to IMQ application, and again 24 h after the 4$^{th}$ IMQ treatment, just prior to euthanasia.

Immunofluorescence (IF) Assays

For IF assays, back skin biopsies were collected post euthanasia, backed with nitrocellulose, embedded in cryomatrix (Tissue-Tek® O.C.T. Compound, Electron Microscopy Sciences) and stored at −80° C. until use. The frozen tissue blocks were sectioned at a thickness of 12 μm on a cryostat (Leica), and collected on microscope slides (VWR® Superfrost®). Slides were allowed to dry at room temperature, and then fixed in 4% PFA in PBS 1× for 10 minutes. Slides were rinsed 5 times with 1×PBS and then blocked for 1 h at room temperature in the following blocking buffer: 5% normal donkey serum, 0.5% bovine serum albumin, 2.5% fish gelatin and 0.3% Triton X-100 in PBS. The slides were incubated with primary antibodies diluted in blocking solution at 4° C. overnight, washed three times with PBS and incubated with secondary antibodies in blocking solution at room temperature for 1 hour. Slides were washed 3 more times with PBS and mounted with ProLong® Gold Antifade Reagent with DAPI (Cell Signaling, #8961). Slides were imaged using Zeiss confocal LSM880. The primary antibodies used were: CD104/b4-INTEGRIN from BD Biosciences, clone 346-11A (1:100), Krt5 from Biolegend #905901 (1:2000), and Krt 10 from Biolegend #905401 (1:500). Alexa Fluor-488, -594 or -647-conjugated secondary antibodies produced in donkey (Jackson Immunoresearch Laboratories) were used. Images were processed and quantifications were performed using HALO 3.0 program.

Skin Histology and Pathology Scoring

Histology and pathology scoring were performed by a licensed veterinarian. Samples were processed, embedded in paraffin, and sectioned at 5 μm, Hematoxylin & Eosin (H&E) staining was performed on a BOND RX autostainer (Leica Biosystems) using standard protocols. After staining, sections were dehydrated and film coverslipped using a TissueTek-Prisma® and Coverslipper film (Sakura). Whole slide scanning (40×) was performed on an Aperio AT2 apparatus (Leica Biosystems). Hematoxylin & Eosin-stained sections of skin from 6-8 week-old female vehicle or IMQ-treated Crnn−/−, +/−, and WT littermates were examined for histomorphological changes related to psoriasis, by implementing semi-quantitative grading scheme that took into account the following seven parameters (Nakajima, K. and Sano, S. (2018), J Dermatol, 45:252-263. doi:10.1111/1346-8138.14112): hyperkeratosis; parakeratosis with hypogranulosis; acanthosis; Munro's microabscess (accumulation of neutrophils in the stratum corneum); inflammatory cell infiltrates (dermis and hypodermis); dilated blood vessels (dermis and hypodermis) and epidermal erosion/ulcer. A 0-4 scoring scale was used: 0-within normal limits, 1-minimal, 2-mild, 3-moderate and 4-severe. A total pathology score was calculated for each mouse by adding the individual histopathological feature scores. A maximum total pathology score of 28 was possible for an individual mouse. Data analysis was performed using GraphPad Prism™ software.

Measurement of Cytokines in Skin Homogenates

Skin samples from vehicle or IMQ-treated Crnn−/−, +/−, and WT littermates were resuspended in tissue protein extraction reagent (T-PER; Thermo Fisher) supplemented with a protease inhibitor cocktail and mechanically homogenized with a TissueLyser II (Qiagen, Hilden, Germany). Total protein content in skin protein extracts was measured by using a Bradford assay (Bio-Rad Laboratories). Myeloperoxidase concentrations in the extracts were measured with the mouse MPO ELISA kit (Hycult Biotech #HK21002) and read on a SpectraMax M5 plate reader (Molecular Devices). Concentrations of all other cytokines were determined by using the V-PLEX Proinflammatory Panel 1 Mouse Kit (MSD #K15048D-1) and a QuickPlex SQ120 plate reader (Meso Scale Discovery, Rockville, Md.).

Results

Figures 2A, 2B, 2C, 2D:
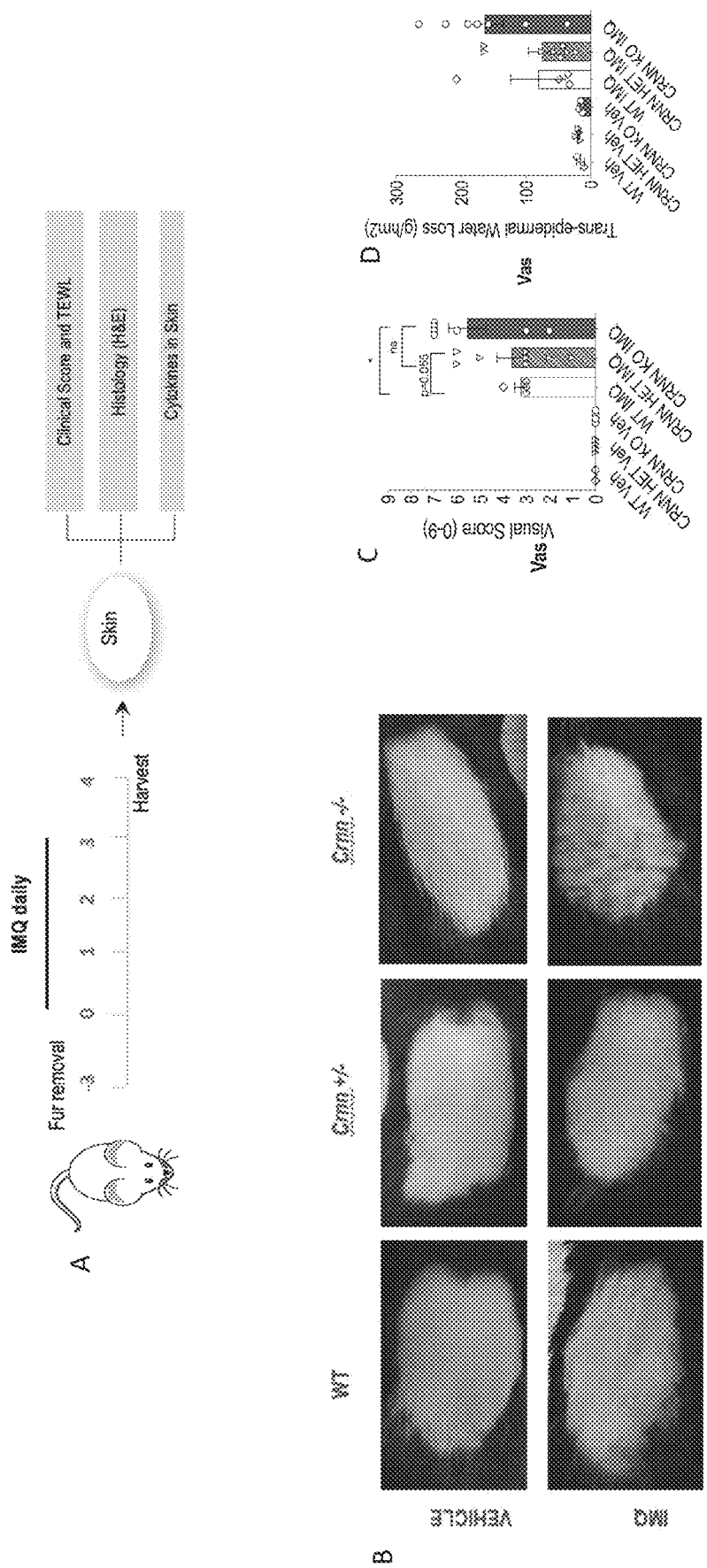
FIGS. 2A-2G. IMQ-induced psoriasis reveals barrier defects in Crnn-/- mice. 2A) Experimental setup of IMQ treatment and skin collection, 2B) Representative photographs of vehicle or IMQ-treated Crnn-/-, +/-, and WT littermates. 2C) Clinical scores and 2D) Trans-epidermal water loss (TEWL) of vehicle or IMQ-treated Crnn-/-, +/-, and WT littermates prior to skin harvest. 2E) Immunofluorescence of Krt10, Krt5, Integrin B4, and DAPI in skin harvested from vehicle or IMQ-treated Crnn-/- and WT littermates. Bar, 100 uM. Quantification of 2E) including average thickness 2F) and average number of nuclei retained 2G) in basal to spinous layers per 250 uM tissue.

Unchallenged, Crnn KO mice did not display any overt spontaneous pathology. In contrast, in a preclinical model of acute IMQ-induced psoriasiform dermatitis that closely resembles human psoriasis lesions in terms of the phenotypic and histological characteristics (L. van der Fits et al., J Immunol 182, 5836-5845 (2009); W. R. Swindell et al., PLoS One 6, e18266 (2011)), Crnn KO mice exhibited exacerbated skin inflammation compared to WT mice. In brief, IMQ was applied daily to the shaved back skin of Crnn KO and WT mice for four consecutive days. By day 5, IMQ-treated Crnn KO mice displayed more severe scaling, erythema and skin thickening compared to WT controls (FIG. 2A). IMQ application resulted in more robust upregulation of pro-inflammatory cytokines (IL-6, IL-1β, TNFα, KC-GRO, IL-36α and IL-36β) in the skin of Crnn KO mice compared to WT controls (FIG. 2B).

Figures 2E, 2F, 2G:
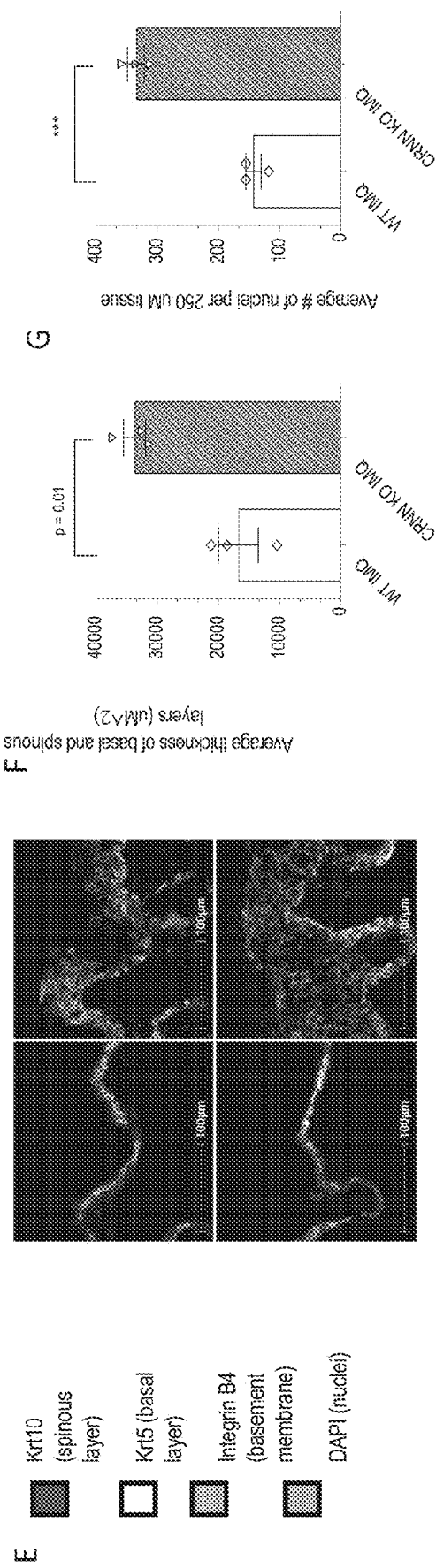

IMQ-induced psoriasis reveals epidermal barrier defects in Crnn−/− mice. To examine how the absence of cornulin impacts skin inflammation, a model of psoriasis was induced using imiquimod (IMQ), a toll like receptor 7 (TLR7) agonist (L. van der Fits et al., J Immunol 182, 5836-5845 (2009); Kanneganti et al. Nature 2006; 440:233-236; Flutter et al., European Journal of Immunology 2013; 43:3138-3146). Briefly, the back skin of Crnn−/−, +/−, and WT littermates was shaved and a depilatory cream was used to thoroughly remove fir, three days prior to IMQ treatment. IMQ or vehicle (unmedicated moisturizing cream) was applied to the back skin daily for 4 days, and skin biopsies were collected post-mortem on day 5 for downstream analyses (FIG. 2A). As previously reported (L. van der Fits et al., J Immunol 182, 5836-5845 (2009)), topical IMQ application resulted in hyperthickening and parakeratosis of the epidermis and upper hair follicles, in addition to a hyperproliferation of epidermal stem cells. Each day, the severity of inflammation was measured using a modified version of the clinical Psoriasis Area and Severity Index. Visual scores for erythema, scaling and thickening were made independently on a scale from 0-3: 0, none; 1, slight; 2, moderate; and 3, marked (FIG. 2B). For all three parameters, Crnn−/− and Crnn+/− mice displayed higher overall severity scores (FIG. 2C) compared to WT littertnates, with Crnn−/− mice showing the most severe phenotype. Trans-epidermal water loss (TEWL), a measure of epidermal barrier integrity, measured according to manufacturer's instructions using a VapoMeter®, was greatest in Crnn−/− mice 24 h after the final IMQ application (FIG. 2D). Immunofluorescent staining of the basal to spinous layers of the epidermis in skin harvested from vehicle or IMQ-treated Crnn−/− and WT littermates revealed, as expected, hyperproliferation in these layers in IMQ-treated samples (FIG. 2E). However, average thickness was significantly increased in IMQ-treated Crnn−/− mice, and was accompanied by a significantly higher retention of nuclei compared to WT controls (FIGS. 2F-G). These data suggest that while Crnn −/− mice have no overt skin abnormalities, IMQ-induced psoriasis reveals that the absence of cornulin may impact the integrity of the epidermal barrier in an inflammatory state.

Figure 3A:
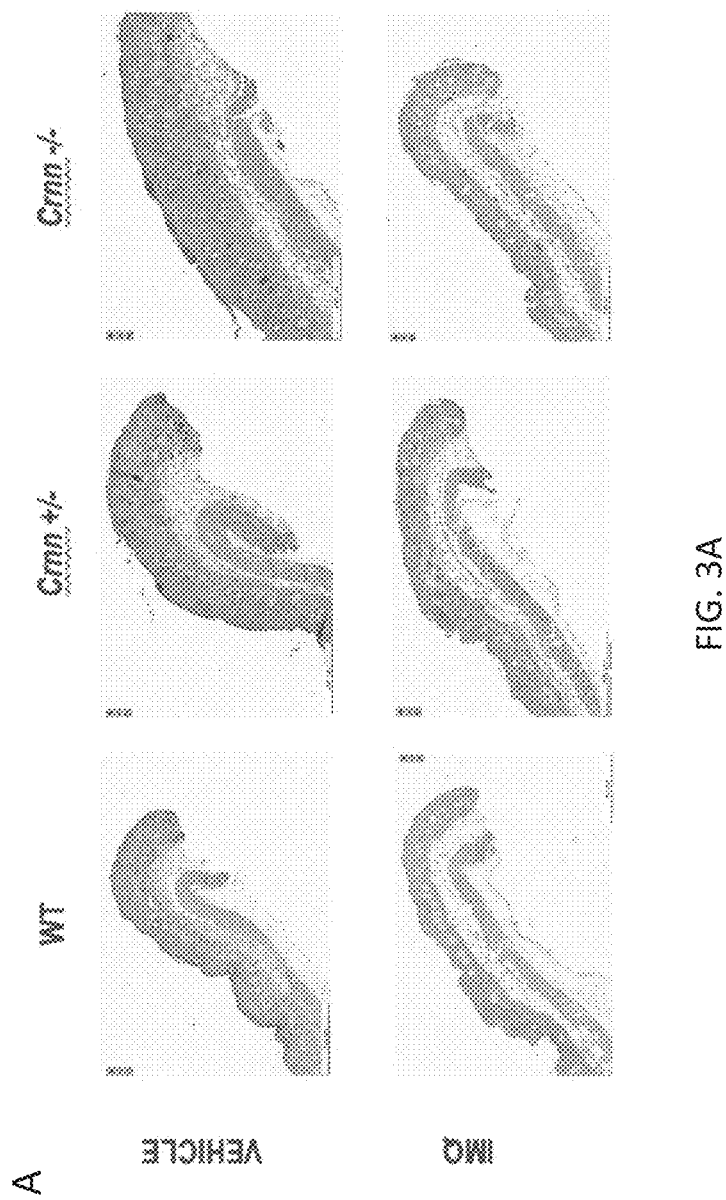
FIGS. 3A-3I. Crnn-/- mice display increased IMQ-induced skin inflammation. 3A) Hematoxylin & Eosin-stained sections of skin from vehicle or IMQ-treated Crnn-/-, +/-, and WT littermates. 3B) Total pathology score of skin from vehicle or IMQ-treated IMQ-treated Crnn-/-, +/-, and WT littermates comprised of a score (0-within normal limits; 1-minimal; 2-mild; 3-moderate; 4-severe) from seven parameters including 3C) acanthosis, 3D) Munro's microabscess, and 3E) parakeratosis with hypogranulosis, 3F) Myeloperoxidase 3G) TNFα 3H) KC/GRO and 3I) II-1β levels in skin harvested from vehicle or IMQ-treated Crnn-/-, +/-, and WT littermates.
Figures 3B, 3C, 3D, 3E:
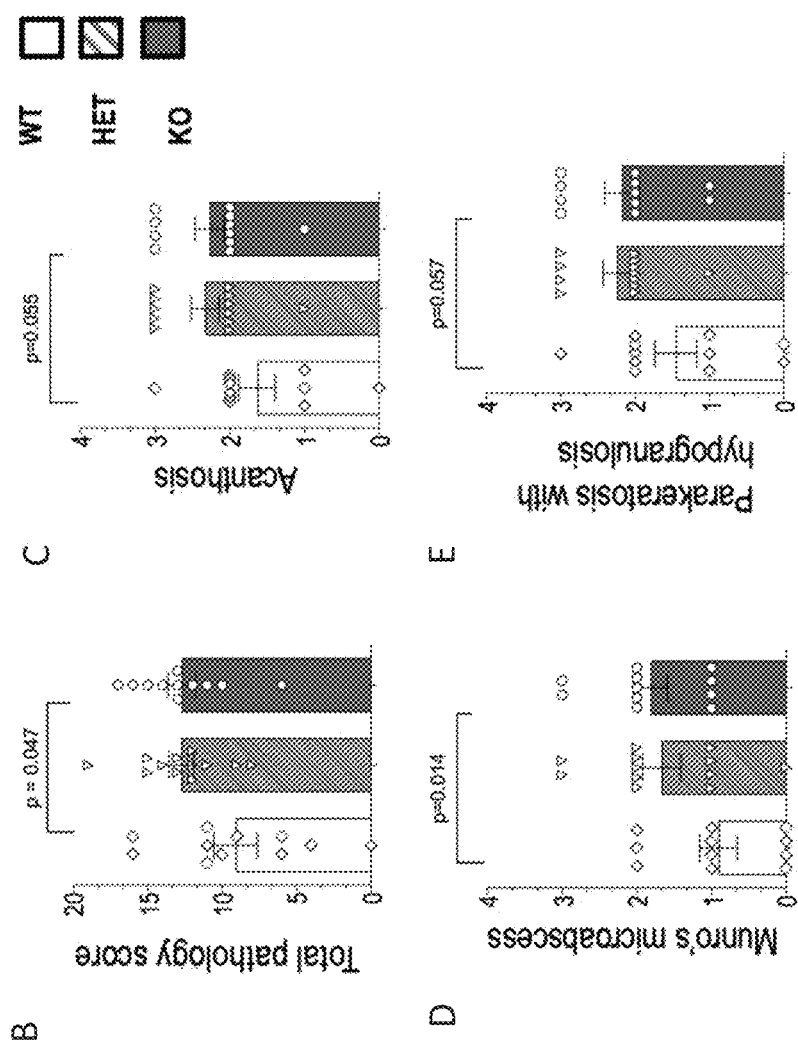
Figures 3F, 3G, 3H, 3I:
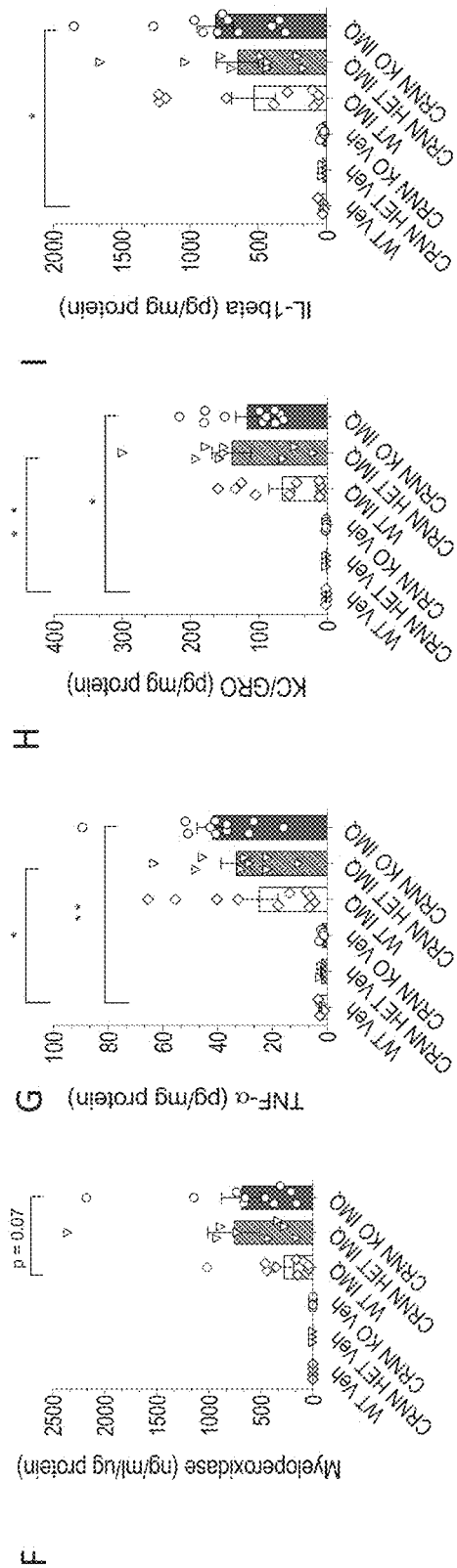

Crnn−/− mice display increased IMQ-induced skin inflammation in vivo. To further characterize the relationship between the integrity of the epidermal barrier and inflammation, a semi-quantitative analysis of Hematoxylin & Eosin-stained sections of skin from vehicle or IMQ-treated Crnn−/−, +/−, and WT littermates were examined by a veterinary pathologist, blinded to genotype, for histomorphological changes related to psoriasis (FIG. 3A). The seven following parameters were examined: hyperkeratosis; parakeratosis with hypogranulosis; acanthosis; Munro's microabscess (accumulation of neutrophils in the stratum corneum); inflammatory cell infiltrates (dermis and hypodermis); dilated blood vessels (dermis and hypodermis) and epidermal erosion/ulcer. The total pathology score was calculated for each mouse by adding the individual histopathological feature scores (from 0-4). The total pathology score was significantly increased in Crnn−/− skin (FIG. 3B). Acanthosis (FIG. 3C); Munro's microabscess, (FIG. 3D), and parakeratosis with hypogranulosis (FIG. 3E) were most adversely impacted in the absence of cornulin. Of note, skin lysates from IMQ-treated Crnn−/− mice showed elevated levels of myeloperoxidase, a marker of neutrophil infiltration consistent with increased numbers of Munro's microabscesses (FIG. 3F), as well as the inflammatory cytokines TNFα (FIG. 3G), KC/GRO (FIG. 3H) and Il-1β (FIG. 3I) compared to WT littermates. These data are consistent with the notion that the absence of cornulin results in increased inflammation in the IMQ-induced psoriasis model.

What is claimed is:

1. A rodent whose genome comprises a loss of function mutation in an endogenous rodent Crnn gene at an endogenous rodent Crnn locus, wherein the mutation comprises a deletion of the sequence beginning from the nucleotide after the ATG start codon through the stop codon of the endogenous rodent Crnn gene, and wherein the rodent is a rat or a mouse.

2. The rodent of claim 1, wherein the Crnn locus comprises a reporter gene coding sequence that is inserted in-frame to the start (ATG) codon of the Crnn locus.

3. The rodent of claim 2, wherein the reporter gene is LacZ.

4. The rodent of claim 2, wherein the reporter gene is selected from the group consisting of luciferase, green fluorescent protein (GFP), enhanced GFP (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, and MmGFP.

5. The rodent of claim 1, wherein the rodent is homozygous for the mutation.

6. The rodent of claim 1, wherein the rodent is heterozygous for the mutation.

7. An isolated cell or tissue of the rodent of claim 1, wherein the genome of the isolated cell or tissue comprises the loss of function mutation in the endogenous rodent Crnn gene at the endogenous rodent Crnn locus.

8. A rodent embryonic stem (ES) cell whose genome comprises a loss of function mutation in an endogenous rodent Crnn gene at an endogenous rodent Crnn locus wherein the mutation comprises a deletion of the sequence beginning from the nucleotide after the ATG start codon through the stop codon of the endogenous rodent Crnn gene, and wherein the rodent ES cell is a rat cell or a mouse cell.

9. A rodent embryo comprising the ES cell of claim 8.

10. A method of making a rodent, the method comprising modifying a rodent genome such that the modified rodent genome comprises a loss of function mutation in an endogenous rodent Crnn gene at an endogenous rodent Crnn locus, wherein the mutation comprises a deletion of the sequence beginning from the nucleotide after the ATG start codon through the stop codon of the endogenous rodent Crnn gene, and obtaining a rodent comprising the modified genome, wherein the rodent is a rat or a mouse.

11. A method of making a rodent, the method comprising introducing a nucleic acid sequence into a rodent ES cell, wherein the rodent ES cell is a rat ES cell or a mouse ES cell, wherein the nucleic acid sequence is integrated into an endogenous rodent Crnn locus in the rodent ES cell and results in a loss of function mutation in the endogenous rodent Crnn gene at the Crnn locus, and wherein the mutation comprises a deletion of the sequence beginning from the nucleotide after the ATG start codon through the stop codon of the endogenous rodent Crnn gene, thereby obtaining a rodent ES cell comprising a modified genome; and
making a rodent comprising the modified genome by using the rodent ES cell comprising the modified genome, wherein the rodent is a rat or a mouse.

12. A method of screening for a compound useful for treating skin inflammation, the method comprising
providing a rodent according to claim 1,
applying imiquimod (IMQ) topically on the skin of the rodent to induce skin inflammation;
administering a candidate compound to the rodent;
measuring skin inflammation in the rodent to determine whether the candidate compound reduces skin inflammation in the rodent.

13. The method of claim 12, further comprising
providing a wild type rodent without the mutation,
applying IMQ topically on the skin of the wild type rodent to induce skin inflammation;
administering the candidate compound to the wild type rodent;
measuring skin inflammation in the wild type rodent; and
determining whether the candidate compound reduces skin inflammation in the rodent with the mutation to the level of the wild type rodent.

* * * * *